United States Patent

Sakai et al.

[11] Patent Number: 5,584,299
[45] Date of Patent: Dec. 17, 1996

[54] HEART PULSE WAVE DETECTING DEVICE USING ITERATIVE BASE POINT DETECTION

[75] Inventors: Yoshio Sakai; Jun Motogi; Sunao Takeda, all of Tokyo, Japan

[73] Assignee: Nihon Kohden Corporation, Tokyo, Japan

[21] Appl. No.: 507,142

[22] Filed: Jul. 26, 1995

[30] Foreign Application Priority Data

Jul. 26, 1994 [JP] Japan .................... 6-173026

[51] Int. Cl.⁶ ..................... A61B 5/022; A61B 5/021
[52] U.S. Cl. ............... 128/681; 128/680; 128/672; 128/677
[58] Field of Search ................. 128/680, 681, 128/677, 672

[56] References Cited

U.S. PATENT DOCUMENTS

| | | | |
|---|---|---|---|
| 4,140,110 | 2/1979 | Jansen et al. | 128/681 |
| 4,154,238 | 5/1979 | Link | 128/681 |
| 4,712,563 | 12/1987 | Link | 128/681 |
| 5,385,149 | 1/1995 | Chang et al. | 128/681 |

*Primary Examiner*—William E. Kamm
*Assistant Examiner*—Carl H. Layno
*Attorney, Agent, or Firm*—Sughrue, Mion, Zinn, Macpeak & Seas

[57] ABSTRACT

A CPU of a control unit receives a blood pressure pulse wave signal, through an AC amplifier and an A/D convertor. The CPU differentiates, for the smoothing of the waveform, the heart pulse wave signal every step of decreasing the pressure in the cuff, thereby detecting a descending zero-cross point m of the differential wave. Further, the CPU detects a slope peak point P' while tracing back from the descending zero-cross point m. The CPU determines the peak points of the pulse wave by using the heart pulse wave signal that is not differentiated. Thereafter, the CPU determines the base points of the pulse wave tracing back from the maximum-slope point, determines the peak value of the heart pulse wave signal in all the steps of decreasing the pressure in the cuff, and finally computes a systolic blood pressure and a diastolic blood pressure.

6 Claims, 9 Drawing Sheets

FIRST DETECTION

SECOND DETECTION

THIRD DETECTION
(SET REFERENCE POINT AS BASE POINT SINCE JUDGING POINT IS OUTSIDE SCOPE)

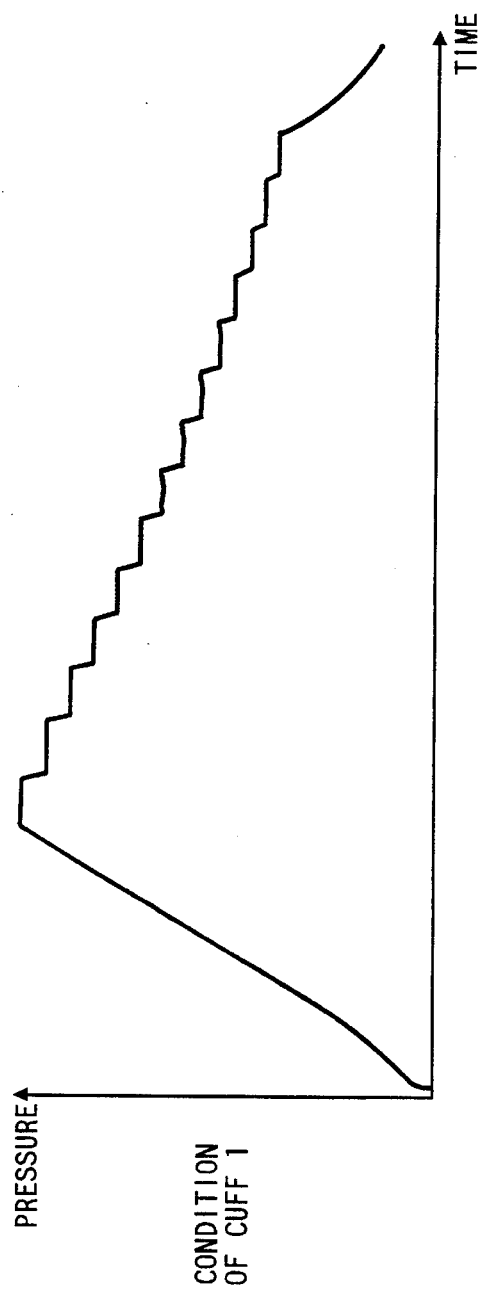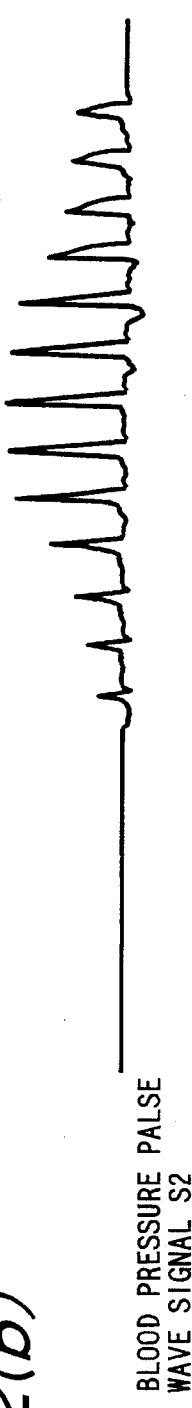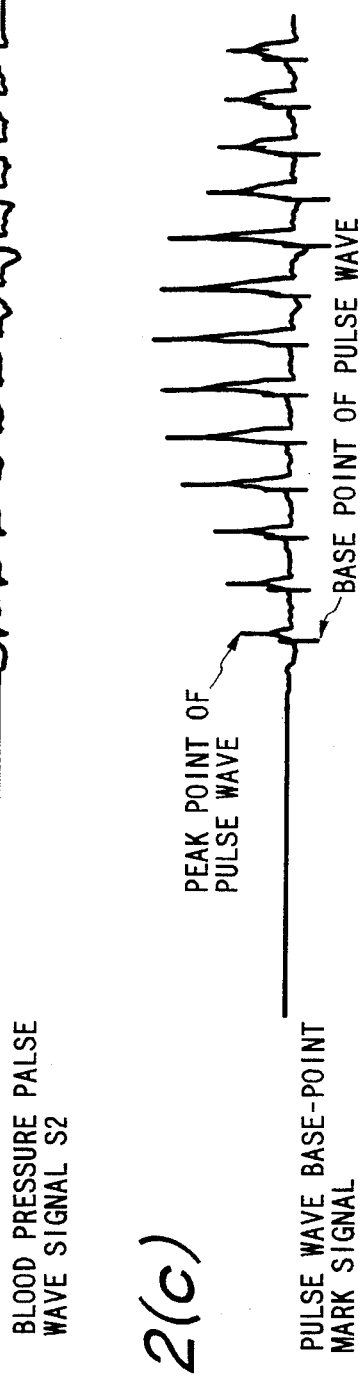
FIG. 2(a)
FIG. 2(b)
FIG. 2(c)

FIG. 4(a)
FIG. 4(b)
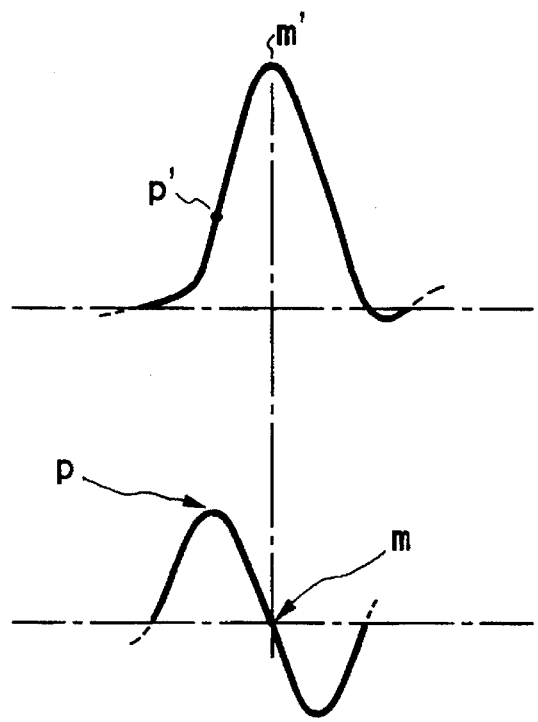
FIG. 9
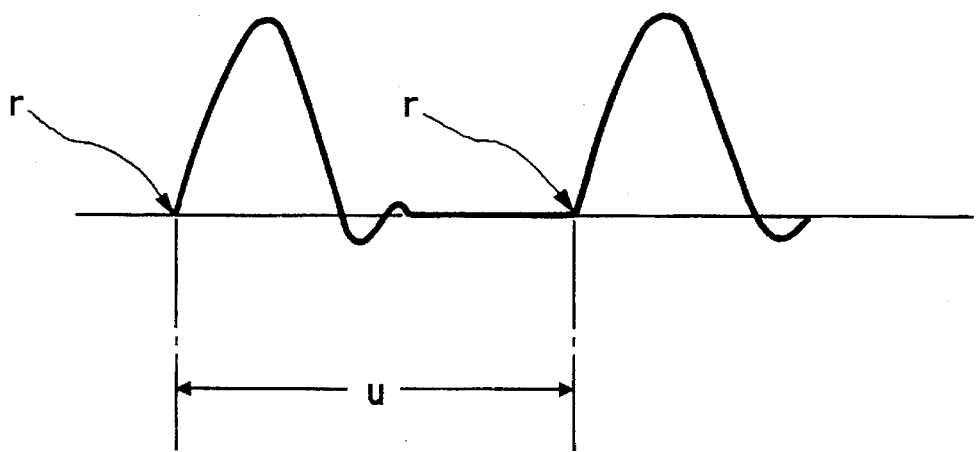

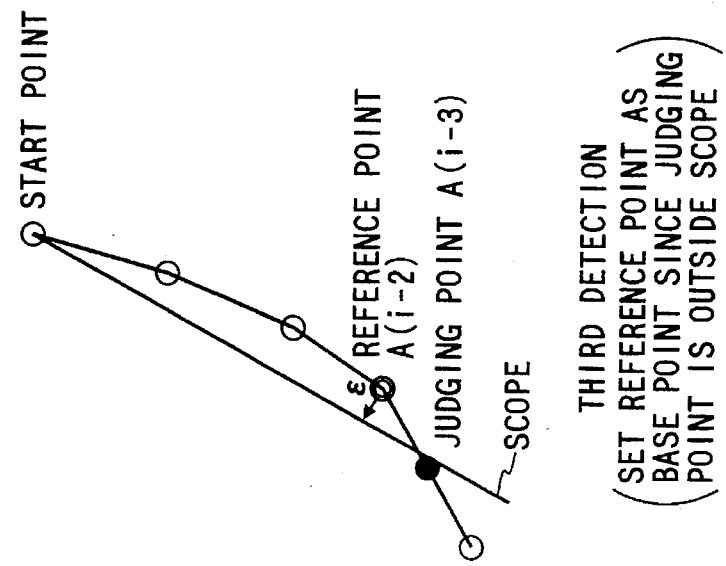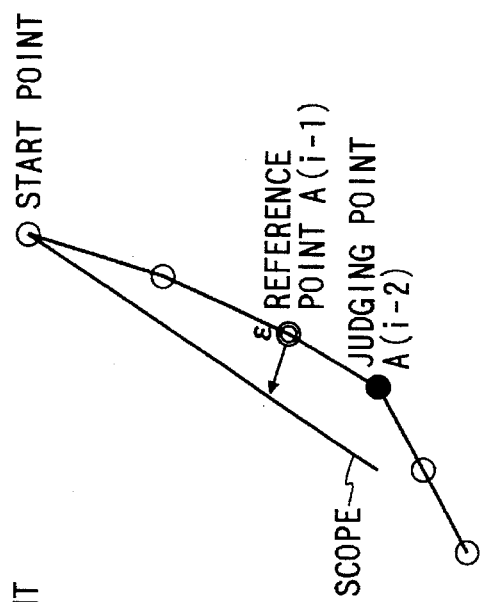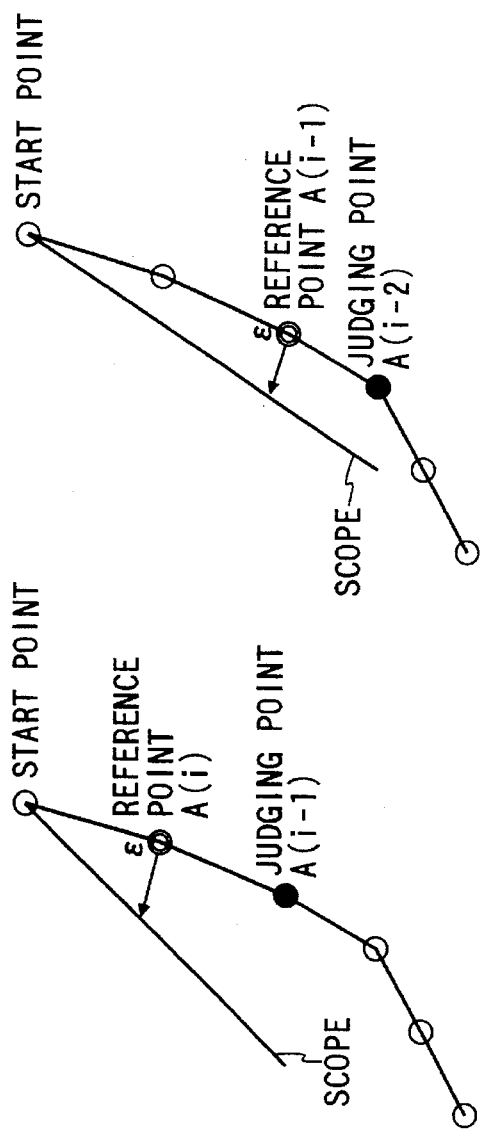

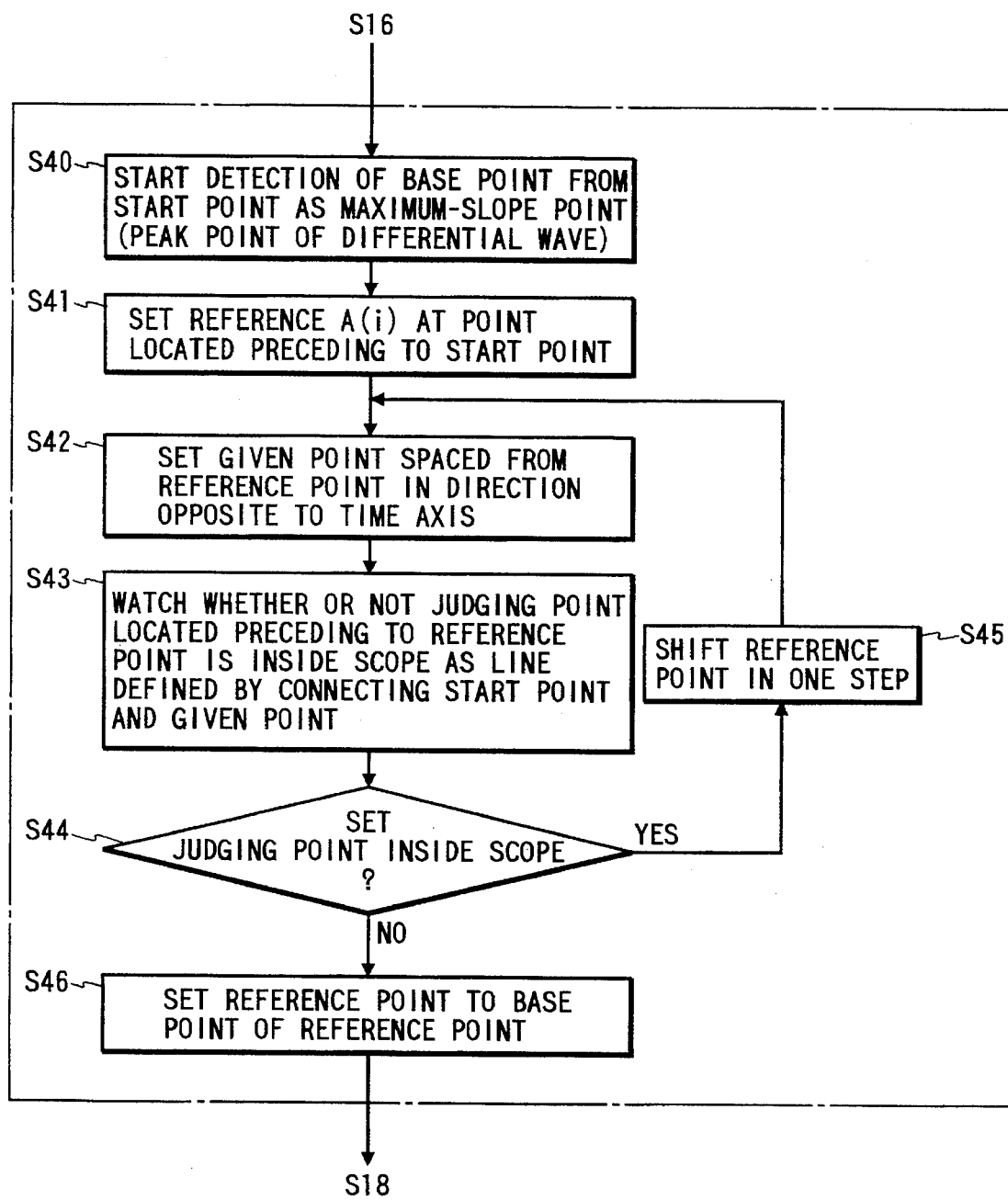

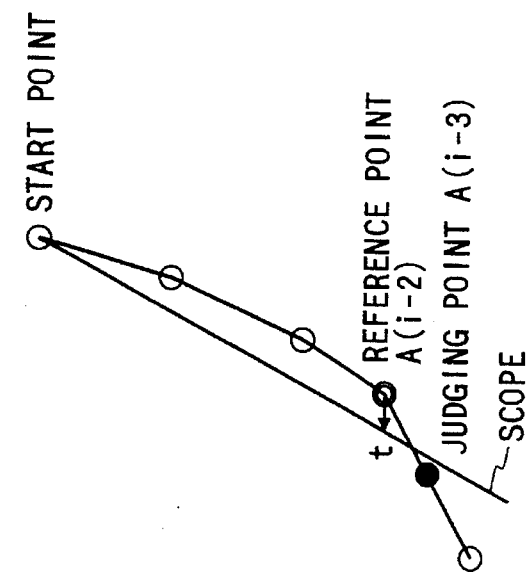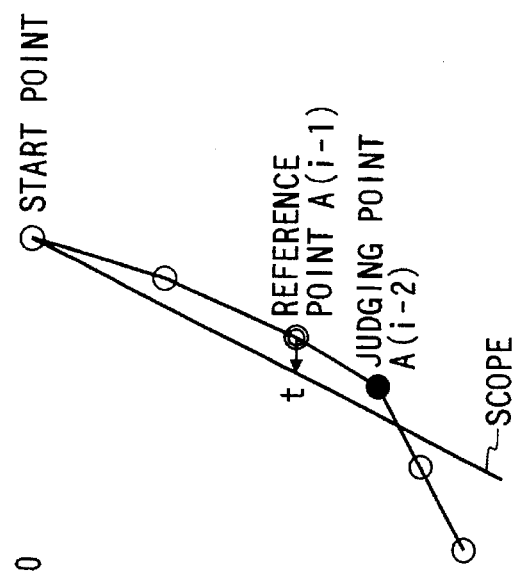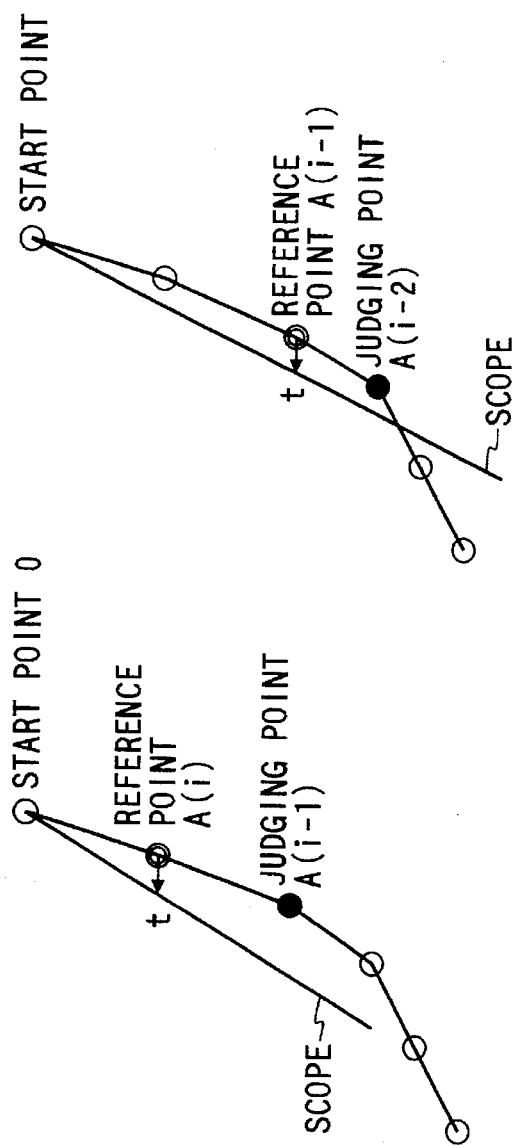

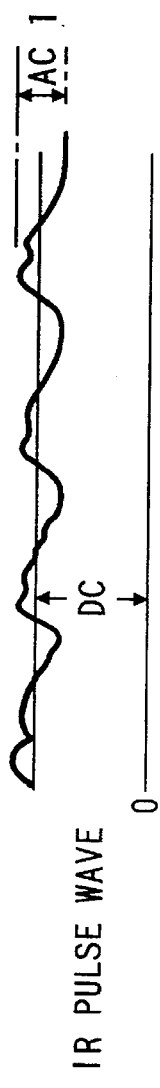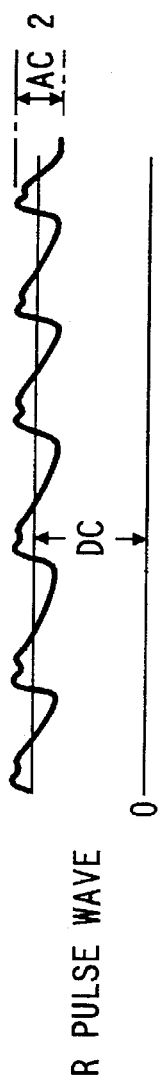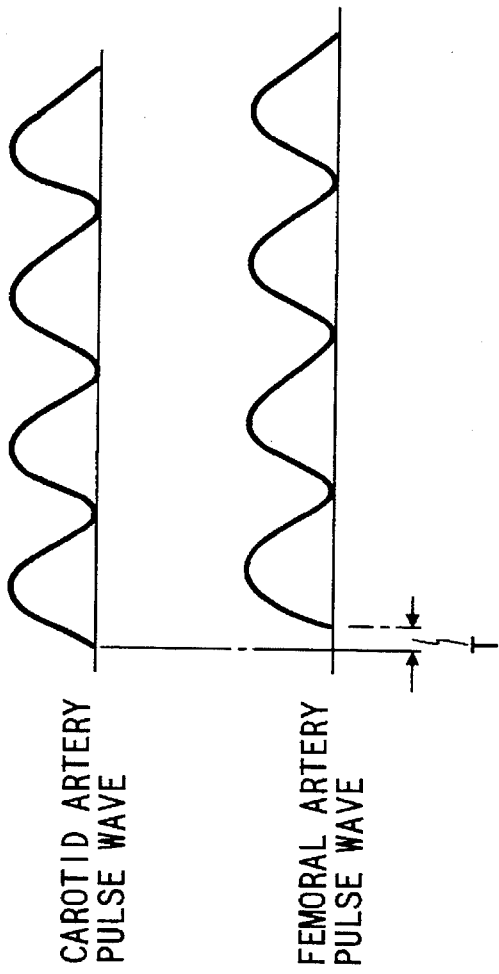
FIG. 10(a)
FIG. 10(b)
FIG. 11(a)
FIG. 11(b)

HEART PULSE WAVE DETECTING DEVICE USING ITERATIVE BASE POINT DETECTION

BACKGROUND OF THE INVENTION

1. Field of the Invention

The present invention relates to a heart pulse wave detecting device for detecting the peak points and the base points of a heart pulse wave when the heart pulse wave is measured, which the device is adaptable for hemadynamometers, blood flow rate measuring device, pulse oximeters, pulse-wave velocity measuring device, and the like.

2. Related Art

An auscultatory method and an oscillometric method are known for the blood pressure measuring methods employed for the blood pressure measuring device. The auscultatory method has the following disadvantages. It is sensitive to noise. The sounds within the body tend to be left out. Sometimes the sounds are left even below the diastolic blood pressure.

In a blood pressure measurement by the oscillometric method which can solve the problem of degrading the blood pressure measuring accuracy, a pulse wave signal representative of a pulsation in an artery is detected in the form of a variation of a pressure in a cuff, and a systolic blood pressure and a diastolic blood pressure are measured on the basis of the pressure variation.

In the blood pressure measurement by the oscillometric method, the systolic blood pressure and the diastolic blood pressure are measured on the basis of a variation of the amplitudes of a heart pulse wave signal. For this reason, the peak points and the base points of a heart pulse wave are measured. In this case, the peak points of the pulse wave are detected for the amplitudes thereof, and a variation of an slope of the pulse wave is detected for the base points of the pulse wave.

The peak points of a heart pulse wave distinctly appears in the waveform. Accordingly, it is easy to reliably detect the peak points. The base points of the heart pulse wave are points where the slope of the waveform is changed in the direction. Because of this, it is difficult to detect the base points.

Particularly, when the cuff pressure transiently fluctuates, drifts, and suffers from noise during the decreasing process of the cuff pressure, problems arisen from such transient variations of the cuff pressure are additionally contained in the waveform data to be computed. This results in exacerbation of the accuracy of specifying the base points, and exacerbation of the accuracy of measuring the systolic blood pressure and the diastolic blood pressure.

SUMMARY OF THE INVENTION

For the above background reasons, an object of the present invention is to provide a heart pulse wave detecting device which is capable of accurately detecting the base points of a heart pulse wave when the heart pulse wave is measured for detecting the peak points and the base points thereof, and the heart pulse wave detecting device improves the accuracy of measuring a systolic blood pressure and a diastolic blood pressure when a blood pressure is measured by a blood pressure detecting device.

To achieve the above object, there is provided a heart pulse wave detecting device for detecting the base points of a heart pulse wave signal and the peak points thereof, comprising: pulse wave detecting means for detecting a pulse wave of a living body; differential means for differentiating a pulse wave outputted from the pulse wave detecting means; first detecting means for detecting a descending zero-cross point of a differential wave differentiated by and outputted from the differential means; second detecting means for detecting a maximum-slope point of the differentiated wave while tracing back from the descending zero-cross point; third detecting means for detecting peak points of the pulse wave outputted from the pulse wave detecting means; and fourth detecting means for detecting the base point of the pulse wave tracing back from the maximum-slope point detected by the second detecting means.

The heart pulse wave detecting device described above is such that the fourth detecting means sets a reference point at a point located preceding to a start point as the maximum-slope point of the pulse wave that is detected by the second detecting means, sets up a distance along a perpendicular to a tangential line at the reference point, and uses a line connecting the start point and the tip of the distance as a scope, checks whether or not a judging point located preceding to the reference point is inside the scope, and if the judging point is located inside the scope, the fourth detecting means shifts the reference point to a point, and repeats a sequence of the step of setting up a distance along a perpendicular to a tangential line at the reference point, and uses a line connecting the start point and the tip of the distance as a scope, and the step of checks whether or not a judging point located preceding to the reference point is inside the scope, and after repeating the sequence of the steps, if the judging point is located outside the scope, the fourth detecting means determines the reference point as a base point of the pulse wave.

The heart pulse wave detecting device described above is such that the fourth detecting means sets a reference point at a point located preceding to a start point as the maximum-slope point of the pulse wave that is detected by the second detecting means, sets a given point at a point spaced from the reference point in the direction that is opposite to the time axis, and uses a line connecting the start point and the time point as a scope, checks whether or not a judging point located preceding to the given point of the reference point is inside the scope, and if the judging point is located inside the scope, the fourth detecting means shifts the given point of the reference point to a point, and repeats the sequential process including the step of setting a given point at a point spaced from the reference point in the direction that is opposite to the time axis, and uses a line connecting the start point and the given point as a scope, and after repeating the sequential process, if the judging point is located outside the scope, the fourth detecting means determines the reference point as a base point of the pulse wave.

The heart pulse wave detecting device described above detects a descending zero-cross point of the differential wave of a heart pulse wave, and detects a maximum-slope point of the heart pulse wave while tracing back from the descending zero-cross point. Further, the heart pulse wave detecting device detects the peak point of the pulse wave, and the base point of the pulse wave tracing back from the detected maximum-slope point. Accordingly, when the peak points and the base points are detected by measuring a pulse wave, the heart pulse wave detecting device can exactly detect the base points of the pulse wave.

A blood pressure detecting device, which incorporates the heart pulse wave detecting device of the invention, can accurately measure a diastolic blood pressure and a systolic blood pressure when it measures a blood pressure. A blood-flow rate measuring instrument, which incorporates the heart pulse wave detecting device of the invention, can accurately measure a flow rate of the discharged blood since the base points of a heart pulse wave are accurately detected and the integration of the continuous pulse wave is performed on the basis of the exact base points.

A pulse oximeter, which incorporates the heart pulse wave detecting device of the invention, can accurately measure the amplitudes of an AC component contained in a detect signal by infrared rays and the amplitudes of an AC component contained therein by red (R) rays of light, since the base points of the pulse wave are accurately measured.

A pulse-wave velocity measuring instrument, which incorporates the heart pulse wave detecting device of the invention, can accurately measure a time difference between the pulse waves in the carotid artery and the femoral artery, viz., a pulse transit time for the same reason.

BRIEF DESCRIPTION OF THE DRAWINGS

FIGS. 2(a) to 2(c) are graphs showing a set of waveforms of a cuff pressure variation, a heart pulse wave signal, and a base-point mark signal;

FIGS. 4(a) and 4(b) are diagrams showing one wave of a heart pulse wave signal and its differentiated wave.

FIGS. 6(a) to 6(c) are diagrams for explaining a process of determining the base points of a heart pulse wave signal by a perpendicular;

FIG. 7 is a flowchart showing a sequence of steps, of a process to determine the base points of the heart pulse wave signal by a time axis;

FIGS. 8(a) to 8(c) are diagrams for explaining a process of determining the base points of a heart pulse wave signal by a time axis;

FIG. 9 is a waveform diagram useful in explaining a heart pulse wave in a blood flow rate monitor;

FIGS. 10(a) and 10(b) are waveform diagrams useful in explaining a heart pulse wave in a pulse oximeter; and FIGS. 11(a) and 11(b) are waveform diagrams useful in explaining a heart pulse wave in a pulse-wave velocity measurement.

DETAILED DESCRIPTION OF THE PREFERRED EMBODIMENTS

A heart pulse wave detecting device according to a preferred embodiment of the present invention will be described with reference to the accompanying drawings.

Figure 1:
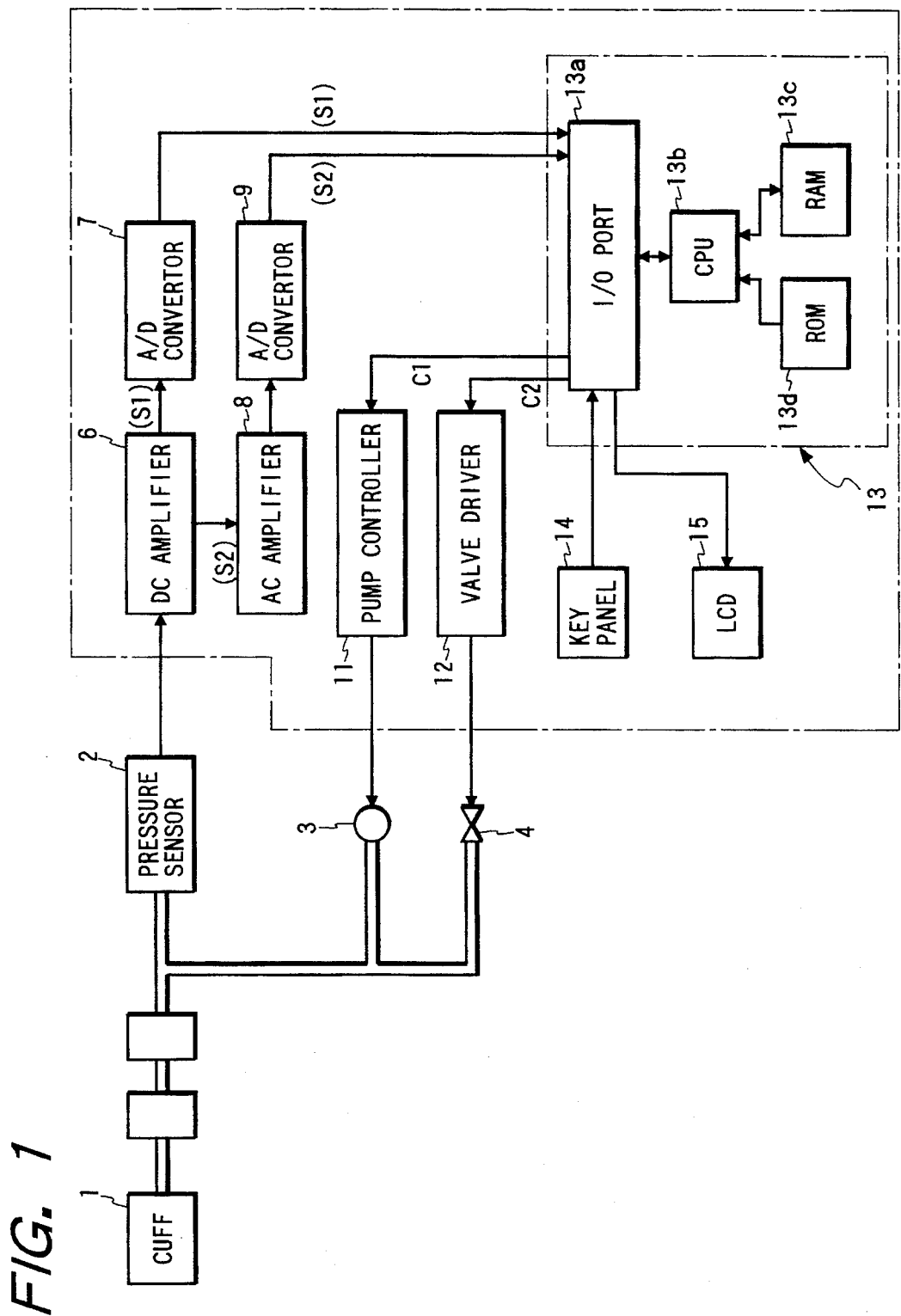
FIG. 1 is a block diagram showing a hemadynamometer incorporating therein a heart pulse wave detecting device according to a preferred embodiment of the present invention.

FIG. 1 is a block diagram showing of a pulse wave detecting device applied to a blood pressure detecting device according to a preferred embodiment of the present invention.

In FIG. 1, the blood pressure detecting means includes a cuff 1 wound around the upper part of an arm or a finger of a subject, a pressure sensor 2 for sensing an air pressure in the cuff 1 and for producing a signal representative of a heart pulse wave, and a pump 3 for feeding air to the cuff 1 to increase a pressure in the cuff 1 up to a value indicated by a control signal C1.

An electromagnetic valve 4 and a DC amplifier 6 are further contained in the hemadynamometer. The electromagnetic valve 4 receives a control signal C2 after the pressure increase process for the cuff 1 is completed, and gradually discharges air from the cuff 1 to decrease the cuff pressure.

The DC amplifier 6 receives a DC pressure signal S1 from the pressure sensor 2 through a low-pass filter (LPF), not shown, and amplifies the pressure signal S1 not containing high frequency noise components.

The blood pressure detecting device further includes an A/D converter 7 and an AC amplifier 8. The A/D converter 7 converts the pressure signal S1 outputted from the DC amplifier 6 into a digital signal. The AC amplifier 8 receives a blood pressure pulse wave signal S2 from the pressure sensor 2, through a band-pass filter (BPF) or a high-pass filter (HPF), both not shown and contained in the DC amplifier 6, and amplifiers the blood pressure pulse wave signal S2. The hemadynamometer additionally includes an A/D convertor 9, a pump controller 11, and a valve driver 12. The A/D convertor 9 converts the blood pressure pulse wave signal S2 outputted from the AC amplifier 8 into a digital signal.

The pump controller 11 controls the feed of air from the pump 3. The valve driver 12 drives the electromagnetic valve 4 to control the discharge of air from the electromagnetic valve 4.

A control unit 13, contained in the blood pressure detecting device, detects the peak points and the base points of a heart pulse wave by processing the pressure signal S1 and the blood pressure pulse wave signal S2 received from the A/D converters 7 and 9, controls the pump 3 by driving the pump controller 11, and controls the decreasing operation of the cuff pressure by discharging compressed air from the cuff 1, through the operation of the valve driver 12.

A key panel 14 and a liquid crystal display (LCD) 15 are further contained in the hemadynamometer.

The key panel 14 are used for instructing the machine to start the detection of the peak points and the base points of a heart pulse wave, and to execute various functions. The LCD 15 visually presents the results of executing the various processes, and processed waveforms.

The control circuit 13 is made up of an I/O port 13a, a CPU 13b, and a RAM 13c as a work memory, and a ROM 13d which stores a control program.

The I/O port 13a receives the pressure signal S1 and the blood pressure pulse wave signal S2 from the A/D convertors 7 and 9, and sends control signals to the pump control circuit 11 and the valve driver 12.

The operation of the heart pulse wave detecting device thus constructed will be described.

Figure 3:
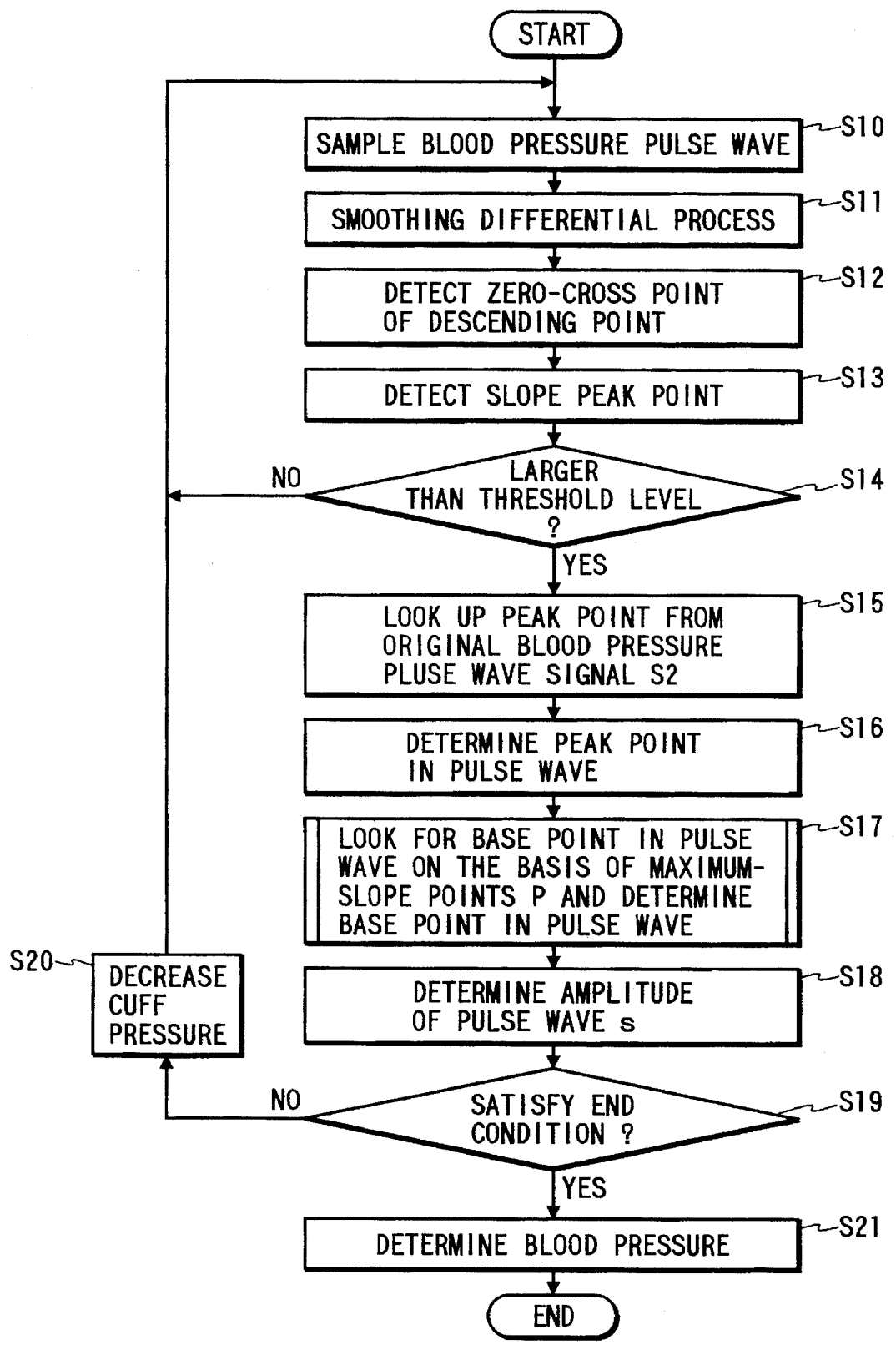
FIG. 3 is a flowchart showing a sequence of steps of a process of measuring a blood pressure by the blood pressure detecting device of FIG. 1.

FIG. 2 is a graph showing a set of waveforms of a cuff pressure variation, a blood pressure pulse wave signal S2, and a base-point mark signal. FIG. 3 is a flowchart showing a procedure of a blood pressure measurement by the blood pressure detecting device of FIG. 1. Referring to FIGS. 1 through 3, the control unit 13 (FIG. 1) controls the pump 3 in response to a signal representing a value set on the key panel 14 to increase a pressure in the cuff 1 (FIG. 2(a)). The control unit 13 also controls the electromagnetic valve 4 for the purpose of the cuff pressure reduction. As a result, a pressure in the cuff 1 is stepwise decreased with time as shown in FIG. 2(a).

The pressure signal S1 representative of a variation of the cuff pressure is derived from the pressure sensor 2, and applied to the CPU 13b of the control unit 13, through the DC amplifier 6 and the A/D converter 7.

The CPU 13b of the control unit 13 receives the blood pressure pulse wave signal S2 from the pressure sensor 2, through the AC amplifier 8, the A/D convertor 9, and the I/O port 13a (step S10).

The CPU 13b differentiates, for the smoothing of the waveform, the blood pressure pulse wave signal S2 received from the pressure sensor 2 every step of decreasing the pressure in the cuff 1. Through the smoothing differential process, the CPU 13b detects a zero-cross point m of the descending part (referred to as a descending zero-cross point) of the differential waveform (FIG. 4(a), and step S11 and S12 in FIG. 3).

Further, the CPU 13b detects a slope peak point P while tracing back from the descending zero-cross point m (FIG. 4(b)), and checks whether or not the slope peak point P is larger than a preset threshold level (threshold value) (step S13 and S14).

If the slope peak point P is smaller than the threshold level (step S14; the answer is NO), the CPU 13b returns to the step S10, and repeats the sequence of the steps thus far carried out. If the slope peak point P is larger than the threshold level (step S14; the answer is YES), the CPU 13b looks up the peak points in the blood pressure pulse wave signal S2, and specifies the peak points (step S15 and S16).

Thereafter, the CPU 13b detects a maximum-slope point P while tracing back from the descending zero-cross point m (FIG. 4(b)), and looks for the base points in the heart pulse wave tracing back from the maximum-slope points P, and determines the base points of the pulse wave (step S17).

Then, the CPU 13b determines the height or amplitude of each pulse wave on the basis of the base points and the peak points that are thus specified (step S18). The CPU 13b judges whether or not the amplitudes of the blood pressure pulse wave signal S2 that are determined at all the steps of decreasing the pressure in the cuff 1 satisfy a predetermined condition of ending the pressure decrease (step S19).

In this embodiment, for example, the predetermined end condition means a state that several waves continuously having the amplitude values a certain ratio, say 50 to 70% of the peak value of the amplitude are detected.

If the end condition is not satisfied (step S19; the answer is NO), the CPU 13b carries out a further pressure decrease (step S20), and returns to the step S10. Then, it repeats the sequence of the steps thus far made. In other words, the CPU 13b determines the amplitudes of the pulse waves of the blood pressure pulse wave signal S2 at all the steps of the cuff pressure decreasing process (step S18).

If the amplitudes of the blood pressure pulse wave signal S2 during the all cuff pressure decreasing process are determined (step S19; the answer is YES), the control circuit 13 directs the valve driver 12 to open the electromagnetic valve 4 to the full.

The thus far gathered data is stored in the RAM 13c of the control unit 13. Then, the control circuit 13 carries out a related process to determine a systolic blood pressure and a diastolic blood pressure (step S21).

The CPU 13b determines the peak points of the waves of the blood pressure pulse wave signal S2 that are detected at all the steps of the cuff pressure decreasing process by differentiating those waves, and then determines the base points of those waves.

The method of determining the base points of the pulse wave signal (step S17 in FIG. 3) will be described.

Figure 5:
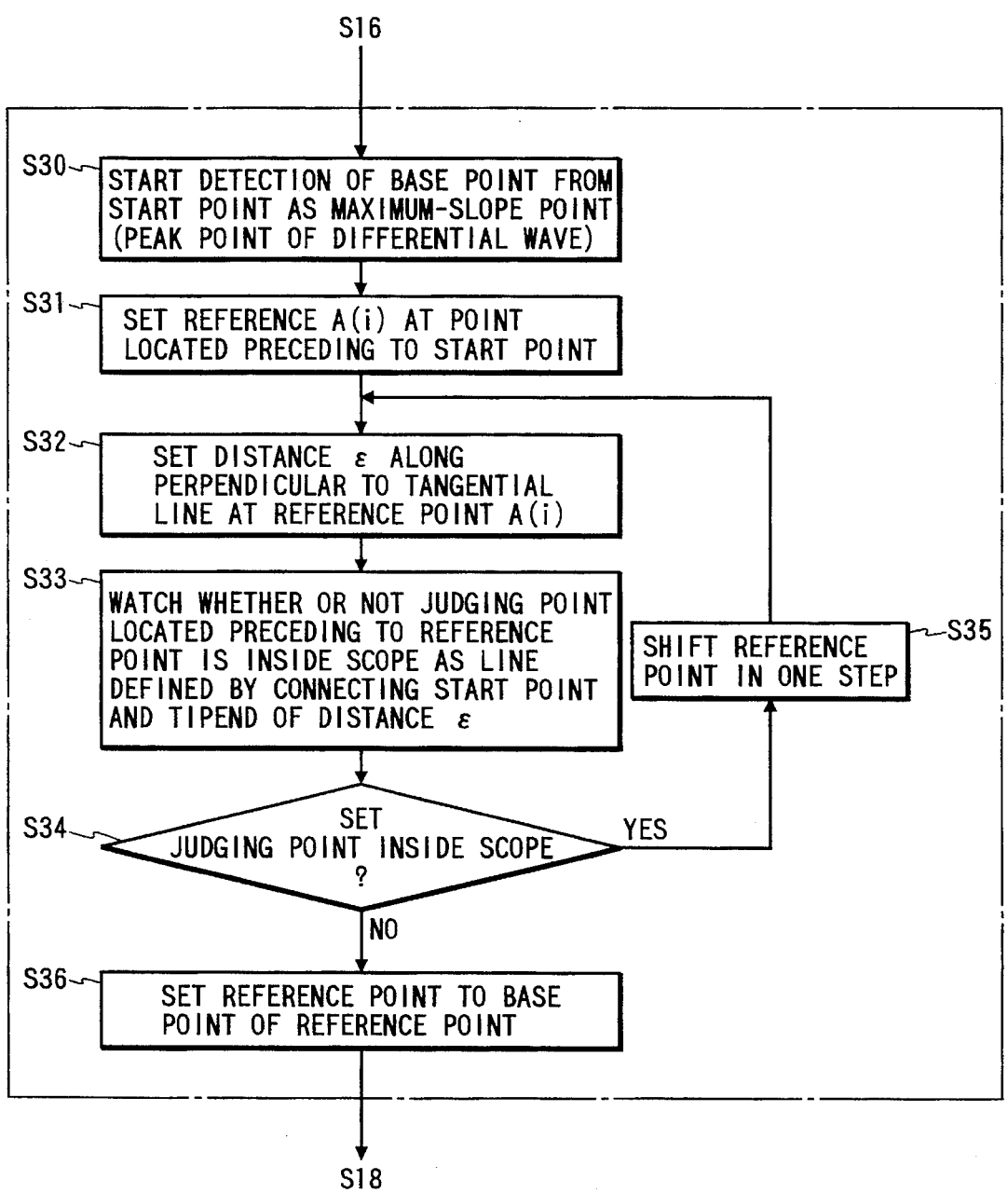
FIG. 5 is a flowchart showing a sequence of steps of a process to determine the base points of the heart pulse wave signal by a perpendicular.

FIG. 5 is a flowchart showing a sequence of steps of a process (subroutine) to determine the base points of the heart pulse wave signal by a perpendicular.

FIG. 6 is a diagram for explaining a process of determining the base points of a heart pulse wave signal by a perpendicular.

After the peak points of the heart pulse wave signal are specified by the process executed by the control unit 13, a first base point detection is performed (FIG. 6(a)). In this detection, detection of a base point of the pressure signal starts, with the maximum-slope point P' (the peak point of the differential wave, FIG. 4) being used as a start-point for the base point detection.

A reference point A(i) is set at a point located preceding to the start point (steps S30 and S31).

A distance $\epsilon$ along a perpendicular to a tangential line at the reference point A(i) is set up in the graph (step S32).

A line connecting the start point and the tip of the distance $\epsilon$ is used as a scope.

The CPU checks whether or not a judging point A(i-1) located preceding to the reference point A(i) is inside the scope (on the lower side of the scope when seen in the drawing) (steps S33 and S34).

A proper distance $\epsilon$, which is for specifying the base point, can be obtained by statistically processing the data of the left ventricular diastole, for example, that are gathered from a number of subjects, although the systolic motion and the diastolic motion of the heart are peculiar to each subject.

If the judging point A(i-1) is located inside the scope (the answer is YES in step S34), the reference point is shifted to a point A(i-1) (FIG. 6(b), step S35). The steps S32 and S33 are executed again. That is, a distance $\epsilon$ is set up, and check is made if the judging point A(i-2) is inside the scope. This sequence is repeated till the judging point goes outside the scope.

If it is outside the scope, viz., the answer is NO (FIG. 6(c), step S34), this reference point is determined as a base point (S36).

FIG. 7 is a flowchart showing a sequence of steps of a process (subroutine) to determine the base points of the heart pulse wave signal by a time axis.

FIG. 8 is a diagram for explaining a process of determining the base points of a heart pulse wave signal by a time axis.

After the peak points of the heart pulse wave signal are specified by the process executed by the control unit 13, a first base-point detection is performed (FIG. 8(a)). In this detection, detection of a base point of the pressure signal starts, with the maximum-slope point P' being used as a start point for the base point detection.

A reference point A(i) is set at a point located preceding to the start point (S40 and S41).

A given point t is set at a point spaced from the reference point in the direction that is opposite to the time axis, in the graph.

A line connecting the start point and the given point t is used as a scope.

The CPU checks whether or not a judging point A(i-1) located preceding to the reference point A(i) is inside the scope (on the lower side of the scope when seen in the drawing) (steps S42, S43, and S44).

If the judging point A(i-1) is located inside the scope (the answer is YES in step S44), the reference point is shifted to a point A(i-2) (FIG. 8(b), step S45). The steps S42 and S43 are executed again. That is, a given point is set at a point spaced from the reference point in the direction that is opposite to the time axis, and check is made if the judging point A(i-2) is inside the scope.

After repeating the sequence of these steps, if it is outside the scope, viz., the answer is NO (FIG. 8(c), step S44), this reference point is determined as a base point (step S46).

In this way, the base points of a heart pulse wave signal can exactly be detected, so that a diastolic blood pressure and a systolic blood pressure can exactly be measured.

The detection of the exact base points of the heart pulse wave is required for other medical instruments. Accordingly, it is evident that the heart pulse wave detecting device of the present invention is applicable for blood flow rate monitors, pulse oximeters, pulse-wave velocity measurement, and the like.

Other applications of the heart pulse wave detecting device of the present invention will be described.

The blood flow rate monitor measures a flow rate of the discharged blood by integrating the waveform of a heart pulse wave for the period u of time between the base points r of a wave and the next wave in a heart pulse wave signal (FIG. 9).

Accordingly, it will readily be understood that the blood flow rate monitor incorporating the heart pulse wave detecting device of the present invention, can exactly measure a flow rate of the discharged blood since the base points of the heart pulse wave are accurately detected.

The pulse oximeter measures the amplitudes of an AC component AC1 contained in a detect signal by infrared rays (IR) (FIG. 10(a)) and the amplitudes of an AC component AC2 contained therein by red (R) rays of light (FIG. 10(b)). Accordingly, it will readily be understood that the pulse oximeter incorporating the heart pulse wave detecting device of the present invention, can exactly measure the amplitudes of the AC components AC1 and AC2.

The pulse-wave velocity measuring instrument measures a time difference T between the pulse waves in the carotid artery and the femoral artery, viz., a pulse transit time (FIG. 11). Also in this instrument, it is required to exactly detect the base points of the heart pulse wave. Because of this, application of the heart pulse wave detecting device of the present invention to the pulse-wave velocity measuring instrument is very useful.

As seen from the foregoing description, the heart pulse wave detecting device of the present invention detects a descending zero-cross point of the differential wave of a heart pulse wave, and detects a maximum-slope point of the heart pulse wave while tracing back from the descending zero-cross point. Further, the heart pulse wave detecting device detects the base point of the pulse wave by using the scope, tracing back from the maximum-slope point.

Accordingly, the detection of the base point of the pulse wave is not affected by disturbance variations in the heart pulse wave. In other words, an exact detection of the base points is ensured even under the condition that the heart pulse wave contains noisy component by disturbance. Thus, the heart pulse wave detecting device of the invention will be applied to a variety of instruments which use the base points of the heart pulse wave for their measurements.

What is claimed is:

1. A heart pulse wave detecting device comprising:
   pulse wave detecting means for detecting a pulse wave of a living body;
   means for differentiating a pulse wave output from said pulse wave detecting means and providing a differentiated wave;
   first detecting means for detecting a descending zero-cross point of said differentiated wave;
   second detecting means for detecting a maximum-slope point of the differentiated wave while tracing back from the descending zero-cross point;
   third detecting means for detecting a peak of the pulse wave output from said pulse wave detecting means; and
   fourth detecting means for detecting the base point of the pulse wave by tracing back from a maximum-slope point on said pulse wave corresponding to the maximum-slope point detected by said second detecting means.

2. A heart pulse wave detecting device according to claim 1, wherein said fourth detecting means comprises:
   means for setting a reference point on said pulse wave at a point located preceding to a start point corresponding to the maximum-slope point on the pulse wave;
   means for setting up a reference distance line along a perpendicular to a tangential line at the reference point, said reference distance line extending from said reference point to an end point;
   means for representing a line connecting the start point and the end point of the reference distance line as a scope;
   means for judging whether or not a judging point located on said pulse wave preceding the reference point is inside the scope; and
   means for shifting the reference point to the judging point if the judging point is located inside the scope while also shifting the judging point to another point on said pulse wave preceding said judging point;
   said reference distance line setting means, said representing means, said judging means, and said shifting means repeat their respective operations until said judging means determines that said shifting means has shifted said reference point to a point outside of a scope represented by said representing means, and said fourth detecting means identifies the reference point outside of the scope as a base point of the pulse wave.

3. A heart pulse wave detecting device according to claim 1, wherein said fourth detecting means comprises:
   means for setting a reference point on said pulse wave at a point located preceding to a start point corresponding to the maximum-slope point on the pulse wave;
   means for setting a given point at a point spaced from the reference point in a direction that is opposite to the time axis along which said pulse wave resides;
   means for establishing a line connecting the start point and the given point as a scope;
   means for judging whether or not a judging point located said pulse wave preceding the reference point is inside the scope; and
   means for shifting the reference point to the judging point if the judging point is located inside the scope while also shifting the judging point to another point on said pulse wave preceding said judging point
   said given point setting means, said representing means, said judging means, and said shifting means repeat their respective operations until said judging means determines that said shifting means has shifted said reference point to a point outside of a scope represented by said representing means, and said fourth detecting means identifies the reference point outside of the scope as a base point of the pulse wave.

4. A heart pulse wave detecting method comprising the steps of:

detecting a pulse wave of a living body;

differentiating said pulse wave to produce a differentiated wave;

detecting a descending zero-cross point of said differentiated wave;

detecting a maximum-slope point of the differentiated wave while tracing back from the descending zero-cross point;

detecting a peak point of the pulse wave; and detecting the base point of the pulse wave by tracing back from a maximum-slope point on said pulse wave corresponding to the maximum-slope point.

5. A heart pulse wave detecting method according to claim 4, further comprising the steps of:

setting a reference point at a point located preceding to a start point corresponding to the maximum-slope point of the pulse wave;

setting up a distance along a perpendicular to a tangential line at the reference point with a line connecting the start point and the tip of the distance as a scope;

judging whether or not a judging point located preceding to the reference point is inside the scope;

if the judging point is located inside the scope, then shifting the reference point to another point, and repeating said step of setting up a distance along a perpendicular to a tangential line at the reference point with a line connecting the start point and the tip of the distance as a scope;

if the judging point is located outside the scope after repeating the setting up step, then determining the reference point as a base point of the pulse wave.

6. A heart pulse wave detecting method according to claim 4, further comprising the steps of:

setting a reference point at a point located preceding to a start point corresponding to the maximum-slope point of the pulse wave;

setting a given point at a point spaced from the reference point in the direction that is opposite to a time axis on which said pulse wave resides, and setting a line connecting the start point and the given point as a scope;

judging whether or not a judging point located preceding to the reference point is inside the scope;

if the judging point is located inside the scope, then shifting the given point of the reference point to another point, and repeating said step of setting a given point at a point spaced from the reference point in the direction that is opposite to the time axis with a line connecting the start point and the given point as a scope, if the judging point is located outside the scope after repeating said given point setting step, then determining the reference point as a base point of the pulse wave.

\* \* \* \* \*